(12) United States Patent
O'Brien

(10) Patent No.: US 10,285,768 B2
(45) Date of Patent: May 14, 2019

(54) VASCULAR CATHETER WIRE CLAMP

(71) Applicant: Joe O'Brien, Alburtis, PA (US)

(72) Inventor: Joe O'Brien, Alburtis, PA (US)

( * ) Notice: Subject to any disclaimer, the term of this patent is extended or adjusted under 35 U.S.C. 154(b) by 102 days.

(21) Appl. No.: 15/340,602

(22) Filed: Nov. 1, 2016

(65) Prior Publication Data

US 2018/0117286 A1  May 3, 2018

(51) Int. Cl.
*A61B 50/20*   (2016.01)
*A61M 5/14*    (2006.01)
*A61B 17/28*   (2006.01)

(52) U.S. Cl.
CPC ........... *A61B 50/20* (2016.02); *A61M 5/1418* (2013.01); *A61B 2017/2808* (2013.01); *A61M 2205/6081* (2013.01)

(58) Field of Classification Search
CPC .............. A61M 25/09041; A61M 2025/09116
See application file for complete search history.

(56) References Cited

U.S. PATENT DOCUMENTS

| | | | | |
|---|---|---|---|---|
| 3,972,333 A * | 8/1976 | Leveen | ................... | A61B 17/30 606/174 |
| 4,390,019 A * | 6/1983 | LeVeen | ................ | A61B 17/122 606/158 |
| 4,896,465 A * | 1/1990 | Rhodes | ................ | A61M 5/1418 128/849 |
| 6,431,864 B1 * | 8/2002 | Silverstein | ................ | A61C 3/10 433/159 |
| 2010/0280544 A1 * | 11/2010 | Banks | ........................ | B25B 9/02 606/210 |

* cited by examiner

*Primary Examiner* — Amber R Stiles
(74) *Attorney, Agent, or Firm* — Barley Snyder (57) ABSTRACT

A vascular catheter wire clamp is provided. The vascular catheter clamp includes an elastic body, a clamping shaft, and a clamping shaft receiving passageway. The elastic body includes a first arm having a first retention surface, a second arm having a second retention surface, and a bent section connecting the first arm and the second arm such that first arm away from the bent section and parallel with the second arm. The clamping shaft extends inward from outward facing surface of the first arm and includes a retention member positioned along an end thereof. The clamping shaft receiving passageway is positioned through the second arm and corresponds with the clamping shaft and the retention member.

17 Claims, 6 Drawing Sheets

VASCULAR CATHETER WIRE CLAMP

FIELD OF THE INVENTION

This invention relates to a wire clamp and, more particularly, to a vascular catheter wire clamp to manage and secure in place various surgical wires, tubing, and coils of wires or tubing.

BACKGROUND

Vascular surgery protocols require securing and managing various medical devices and accessories. In such surgery, patients are positioned in such a way as to permit a surgeon and other medical personnel access to the portion of the body that will be operated on. The patient's body is draped under sterile coverings and all equipment maintained as sterile throughout the procedure. In particular, vascular surgery protocols involve manipulating wires and tubing through catheters, requiring positioning and securing without crimping, bending, or damage. Additionally, wires and tubing need to be positioned to avoid strain or tension along their length during and after the protocol. To avoid such strain or tension, a length of wire or tubing can be gathered and stored in a coil, secured, and drawn upon as needed during and after the surgical procedure.

There are several disadvantages with the known equipment for securing and managing these surgical wires, tubing, and coils. The known equipment often is difficult to operate with one hand and is therefore awkward to open, engage, and close. Previously known equipment constructed of multiple parts may fail in use. The clamping surfaces not designed to spread a clamping force evenly may not prevent crimping, bending, and damage to the wires, tubing, and coils. Equipment that crimps, bends, or damages a wire, tubing, or coils complicates and prolongs the surgical procedure, adding time and expense to the surgery to reposition or replace elements.

SUMMARY

A vascular catheter wire clamp is provided. The vascular catheter clamp includes an elastic body, a clamping shaft, and a clamping shaft receiving passageway. The elastic body includes a first arm having a first retention surface, a second arm having a second retention surface, and a bent section connecting the first arm and the second arm such that first arm away from the bent section and parallel with the second arm. The clamping shaft extends inward from outward facing surface of the first arm and includes a retention member positioned along an end thereof. The clamping shaft receiving passageway is positioned through the second arm and corresponds with the clamping shaft and the retention member.

BRIEF DESCRIPTION OF THE DRAWINGS

The invention will now be described by way of example with reference to the accompanying figures, of which.

DETAILED DESCRIPTION OF THE EMBODIMENT(S)

The invention is of particular use with a catheter, a device through which vascular wire is threaded into a patient for various purposes. Catheters typically extend through the patient's skin and are coupled with external diagnostic or therapeutic equipment (leads, guidewires, stylets, and the like) or are used to introduce other elongated medical instruments or fluids or the like, or to withdraw fluid or to measure pressure, or the like, through a lumen opened at the accessed surgical site. The terms "catheter" and "lead" are often interchanged in these and other contexts.

Definitions:

Before describing the present invention in detail, several terms used in the context of the present invention will be defined. Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. Any and all publications, patents, and other references mentioned herein are incorporated by reference in their entireties for all permitted purposes As used herein, the term "proximal" designates the end of a component which is nearer to an operator when in use, e.g. a physician controlling the apparatus. The term "distal" designates the end of a component that is further away from an operator when in use.

"Wire" designates any suitable elongate element of metal, plastics, or any other suitable material(s). It may have any suitable size and shape and may have a cross-section which is constant or which varies along its length and may be circular or non-circular, such as elliptical, square, rounded off, square, or polygonal. The wire may be solid or hollow.

Guidewires are small diameter wires that are directed through tortuous pathways to provide for advancement of open-ended medical leads or catheters having guidewire receiving lumens over-the-wire. Certain guidewires are also designed to function as a micro-catheter for infusion of fluids through a guidewire lumen. Other guidewires include insulated electrical conductors connected at the guidewire proximal end with an external medical device to deliver electrical energy for tissue stimulation or to conduct electrical signals of the body to the external medical device.

Figure 1:
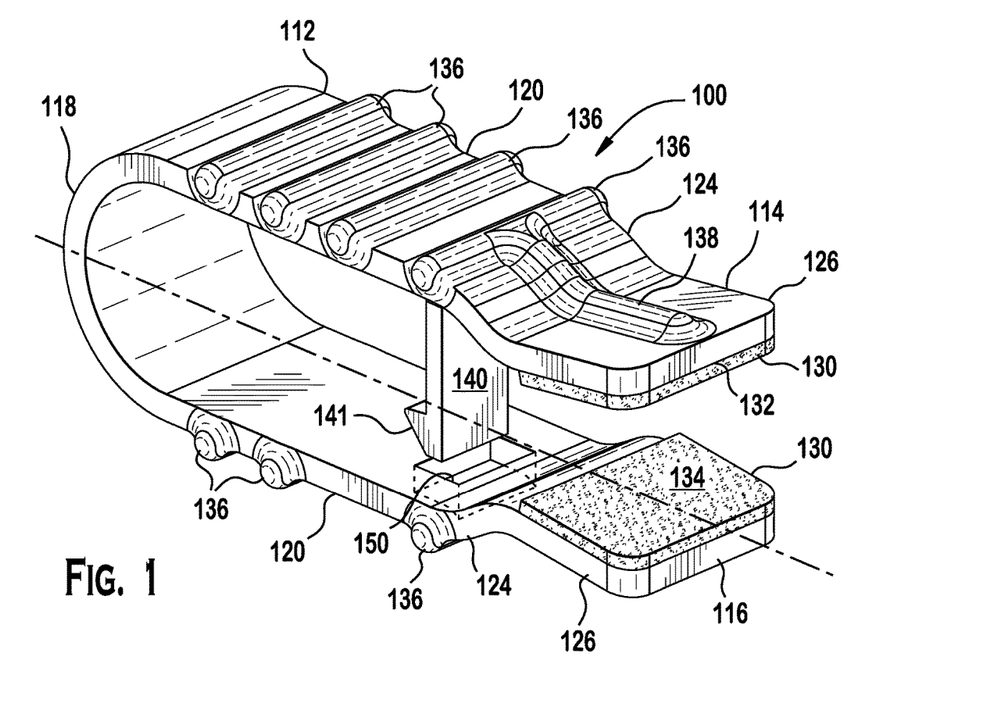
FIG. 1 is a perspective view of a vascular catheter wire clamp according to the invention and shown in an open position.
Figure 2:
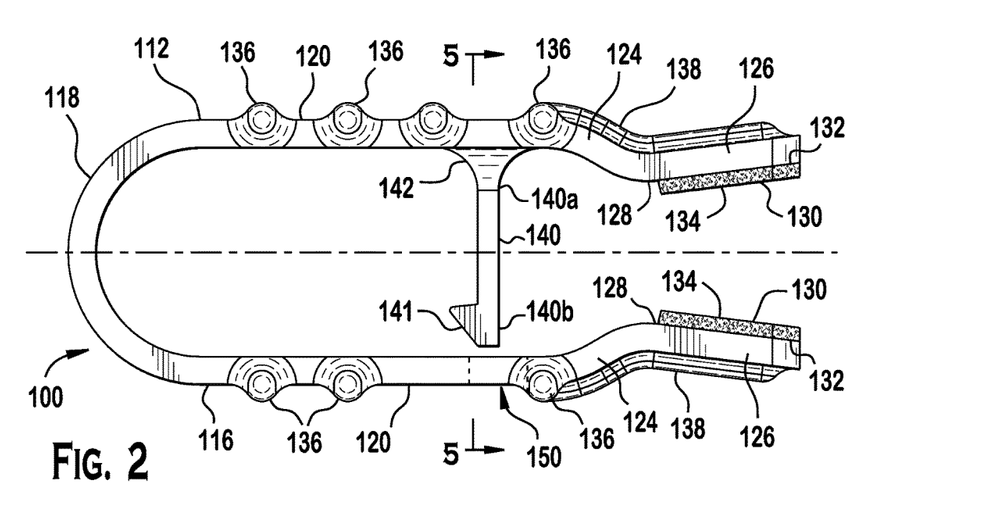
FIG. 2 is a side view of the vascular catheter wire clamp of FIG. 1.
Figures 3, 4:
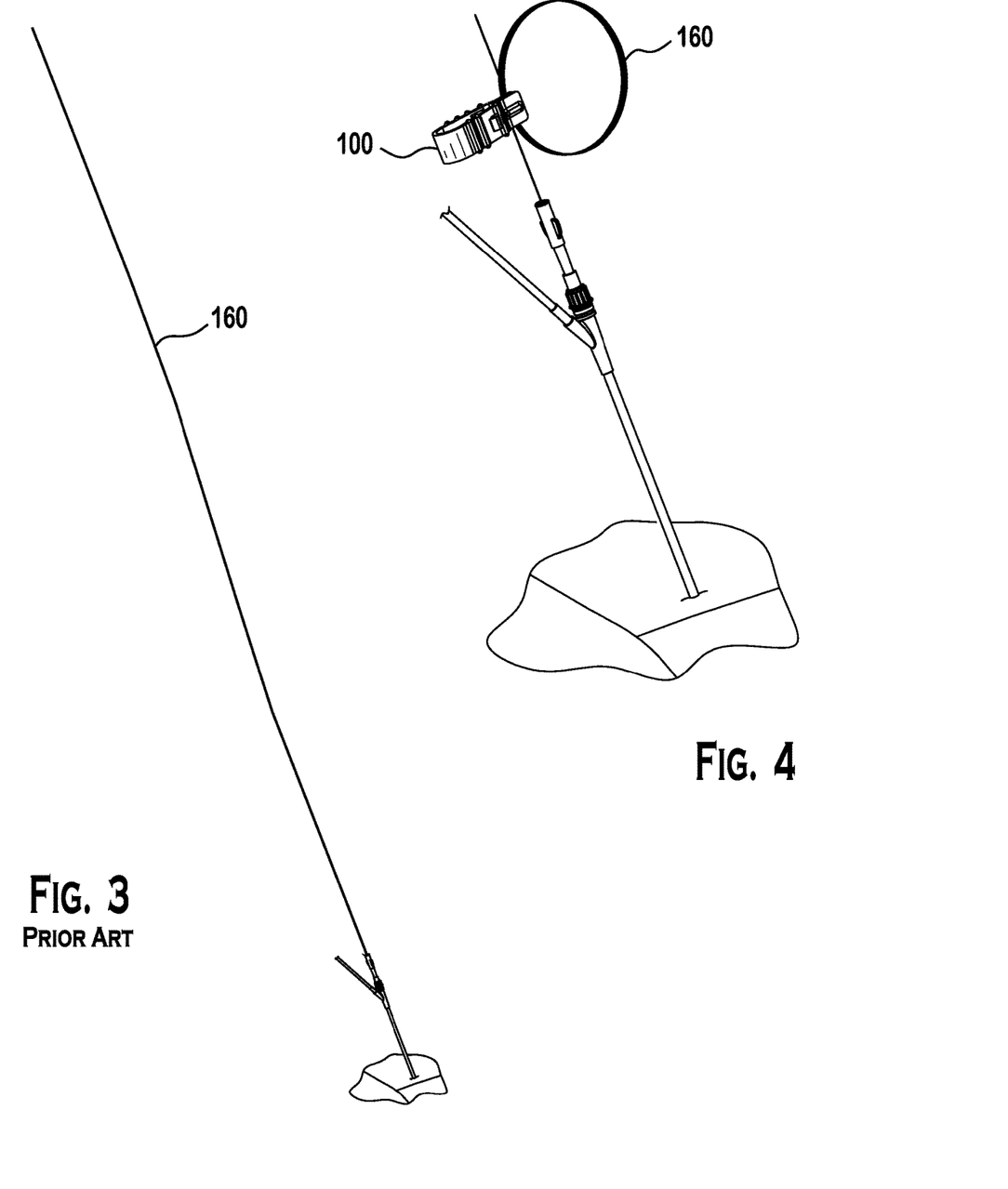
FIG. 3 is a perspective view showing known vascular catheter wires in use.
FIG. 4 is a perspective view showing a vascular catheter wire clamp according to the invention in use to contain a known vascular catheter wire.

Referring first to FIGS. 1 and 2, a vascular catheter wire clamp 100 (hereinafter referred to as "clamp 100") according to the invention is shown.

As shown in the Figures, the clamp 100 generally includes a body 112 having two opposing planar surfaces. In the shown embodiment, the body 112 is a solid, monolithic member and is generally rectangular shaped. However, one skilled in the art should appreciate that the body 112 could be formed in various polygonal shapes that permit the function and operation of this invention, as disclosed and claimed.

In an exemplary embodiment, the body 112 is formed from an elastic plastic and formed into a "U"-shape monolithic member. The body 112 includes a first arm 114 and a second arm 116 of generally equal lengths and connected by a bent section 118. As such, distal ends of the first arm 114 and of the second arm 116 are positioned to correspond with each and positioned opposite the bent section 118. Since the body 112 is "U"-shaped and elastic, distal ends of the first arm 114 and of the second arm 116 are movable toward and away from each other.

The body 112 is semi-rigid, solid, and monolithic in the shown embodiments. The body 112 is preferably extruded or injection molded using a moldable material, such as polypropylene. One of ordinary skill in the art would appreciate that the body 112 may be prepared from other structural materials including other polymers, such as acrylonitrile butadiene styrene, polyethylene, polyester, polystyrene, polyvinyl chloride, or other known thermoplastics or thermosets. In addition, the body 112 may be made from other materials such as metal, metal alloys, material composites, or other suitable materials known in the art that supply the needed characteristics to the clamp 100. The body 112 may alternatively be manufactured through casting, stamping, or other method known to one of skill in the art and consistent with the chosen material to achieve the desired characteristics for its intended use.

In the shown embodiment, each of the first arm 114 and the second arm 116 includes a clasping section 120, a bridge section 124, and a retention section 126, Each clasping section 120 is an elongated member and extends from one of the ends of the bent section 118. As shown, each clasping section 120 is positioned parallel to the other and extends away from the bent section 118. In the exemplary embodiment shown, each clasping section 120 is angled at approximately 30 degrees, away from a longitudinal axis L of the body 112.

In the shown embodiment, each of the first arm 114 and the second arm 116 includes a bridge section 124. Each bridge section 124 extends from one of the two clasping sections 120 and is angled toward a longitudinal axis L of the body 112. In the shown embodiment, each bridge section 124 is angled inward, toward the longitudinal axis L of the body 112. In an exemplary embodiment, each bridge section 124 is angled at approximately 30 degrees inward, toward the longitudinal axis L of the body 112.

As shown, each retention section 126 is an elongated member that extends from one of the ends of the pair of bridge sections 124. The retention sections 126 are positioned opposite ends of the body 112 than the bent section 118 and include inner planar surfaces. These inner planar surfaces are retention surface 128 for the first arm 114 and the second arm 116 and positioned such that they face each other in the embodiment shown. Since the body 112 is formed into "U"-shaped member, the retention sections 126 are generally positioned to correspond with each other. Each retention section 126 is angled with respect to a longitudinal axis L of the body 112. In the exemplary embodiment shown, each retention section 126 is angled at approximately 30 degrees, away from the longitudinal axis L of the body 112. When the clasping section 120 is squeezed, the elastic body 112 is compressed, the first arm 114 and the second arm 116 come together, and each retention section 126 is pushed toward the other and the retention surfaces 128 positioned parallel to each other.

In the shown embodiment, the retention surfaces 128 are rectangular-shaped planar members in the embodiment shown. Each retention surface 128 includes a gripping pad 130 attached thereto.

Each gripping pad 130 is a rectangular-shaped planar member of generally the same length and width as the retention surface 126 and has an inward-facing gripping surface 132 and an outward-facing attachment surface 134. The total height of the gripping pads 130 is such that wires 160 are secured and prevented from contact with or damage from the retention surface 128 during use of the clamp 100.

To ensure connection between retention surface 126 and gripping pad 130, the outward-facing attachment surface 134 is constructed with materials or textures complementary to those of the inward-facing surface of the retention surfaces 128, as may be known to one of ordinary skill in the art. Each gripping pad 130 is made of compressible foam, cork, or other material suitable for the function and operation of clamp 100. To be suitable for this use, a material can be sterilized. The choice of these materials or textures may additionally permit the replacement of the gripping pad 130. In one embodiment, the height of each gripping pad 130 is approximately 0.125 inch. These materials may therefore further include an adhesive layer. One example of the gripping pad 130 may be an adhesive foam pad (such as those manufactured by 3M Corporation). Alternatively, the inward-facing gripping surface 132 and an outward-facing attachment surface 134 may accommodate an attachment means consisting of two strips of nylon fabric, one having tiny hooked threads and the other a coarse surface, that form a strong bond when pressed together.

When the clasping section 120 is squeezed, the elastic body 112 is compressed and forces A and B are applied on the first arm 114 and on the second arm 116, the two retention surfaces 126a 126b (accommodating the total height of gripping pads 130) meet along a longitudinal plane along the longitudinal axis L of the body 112.

As shown in the Figures, a plurality of gripping supports 136 are arranged crosswise, across a width of the body 112. Additionally, the plurality of gripping supports 136 are positioned on the outward facing surface of each of the first arm 114 and the second arm 116 between the bent section 118 and bridge section 124. The use of gripping supports 136 enables easier and more convenient one-handed operation of clamp 100. The gripping supports 136 may be surface textures, features, or added layers. A particular preferred gripping support 136 is a finger bar directing the forces A and B to move clamp 100 into a closed and locked position.

At least one reinforcement rib 138 is located on the outward facing surface of each retention surface 128 and is oriented longitudinally on each retention surface 126 and bridge section 124 from the distal end of each arm 114, 116 towards the plurality of gripping supports 136. The at least one reinforcement rib 138 function to evenly distribute the force applied to operate clamp 100 to grip the wire 160.

With reference to FIGS. 1-2, and 5-12, a clamping shaft 140 is connected on a first end 140a to the inward-facing surface of first arm 114 at a point located near the distal end of clasping section 120 and the gripping supports 136, as well as the proximal end of bridge section 124. In the shown embodiment, an inner support 142 may be positioned between the inward facing surface of first arm 114 and the first end 140a of clamping shaft 140. Inner support 142 may be added to increase the stability of the attachment of clamping shaft 140 to first arm 114.

As seen in FIGS. 1-2, and 5-12, a retention member 141 is on clamping shaft 140 at a second end 140b. The retention member 141 is positioned and dimensioned to pass through an opposite receiving passageway 150 located on the second arm 116 upon the application of forces A and B on clamp 100. One skilled in the art should appreciate that the retention member 141 and the receiving passageway 150 can be positioned on either arm 114, 116.

It is expected that the clamp 100 may be scaled in various sizes to accept wires 160 of different dimensions for use in different applications. The use of such relatively larger or smaller clamps 100 will be the same regardless of the specific application. Additionally, the material used to manufacture clamps 100 may be coded in colors standardized for a particular size or application. The standardized colors communicate the identity or purpose of the particular wire 160 associated with a particular clamp 10.

In the shown embodiments, the body 112 is elastic so that arms 114, 116 may flex and deflect with respect to the bent section 118. The first arm 114 and the second arm 116 are temporarily displaceable with force directed simultaneously on the outer surface of the first arm 114 and the outer surface of the second arm 116. The first and second arms 114, 116 return to their original positions and configuration upon the release of the applied force as disclosed below. One of ordinary skill in the art should appreciate that other embodiments are possible. For example, arms 114, 116 and the bent section 118 may be thicker or thinner, so that the clamp 100 provides more or less rigidity and support. The desired thickness of the first arm 114, the second arm 116, and the bent section 118 may also depend on the particular molding materials used for the body 112.

In the shown embodiment, the outer surface of the first arm 114 and the outer surface of the second arm 116 are formed to have a plurality of gripping supports 136. The gripping supports 136 may be formed by means of creating an irregular surface or roughening the surface. This supplemental friction may be created during molding, during post-manufacturing, or by adding an element such as a friction bar or surface layer to the outer surfaces of the first and second arms 114, 116.

Now with reference particularly to FIGS. 3-4, and 7-12, an exemplary use of clamp 100 will be described. The clamp 100 is generally used to organize, secure, and maintain a degree of desired tension in wires 160 related to surgical procedures. The clamp 100 may be of use in medical or veterinary procedures.

Figure 5:
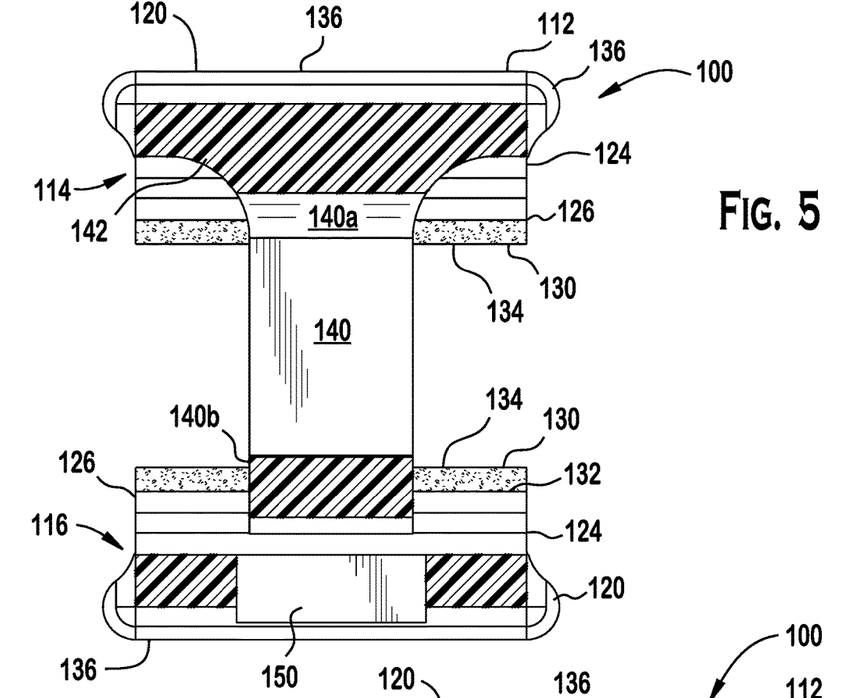
FIG. 5 is a cross section view of the vascular catheter wire clamp of FIG. 2 taken along line 5-5 and shown in an open and unlocked position.
Figure 6:
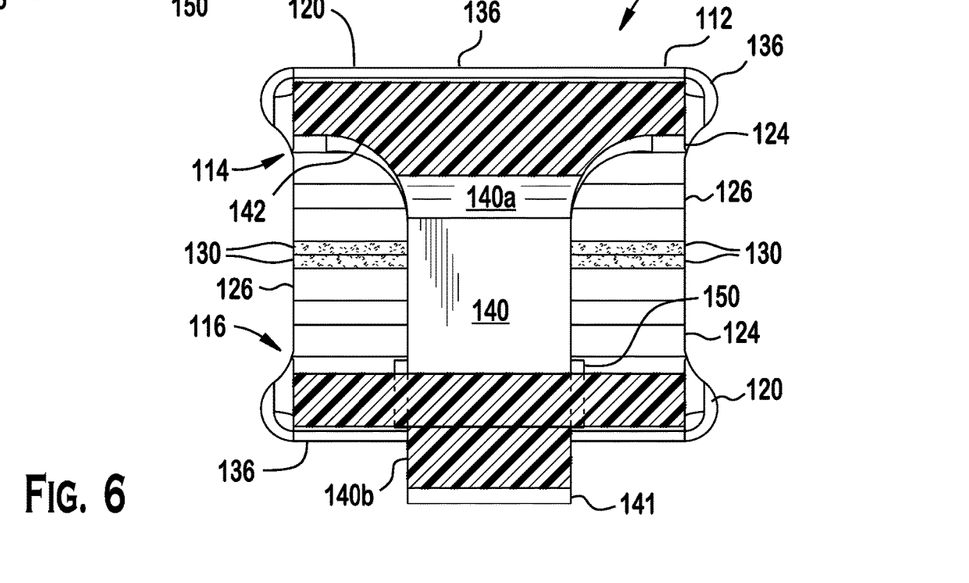
FIG. 6 is a cross section view of the vascular catheter wire clamp of FIG. 2 taken along line 5-5 and shown in a closed and locked position.

In any embodiment of the invention, an operator exerts forces A and B simultaneously on the outer surface of the first arm 114 and the outer surface of the second arm 116 deflect the arms 114, 116 inwardly to cause the retention member 141 and adjacent portion of the clamping shaft 140 to enter the receiving passageway 150. FIGS. 5 and 6 are cross sections of clamp 100 through the clamping shaft 140 showing how an operator effects this deflection. The exerted forces A and B cause a ledge 141a of the retention member 141 to pass through the receiving passageway 150 and to clear the level of the outer surface of the second arm 116, whereby deflection of the clamping shaft 140 catches the retention member 141 on the proximal and the outer edge 151 of the receiving passageway 150. In this configuration, the wires 160 are thus securely gripped.

Figure 7:
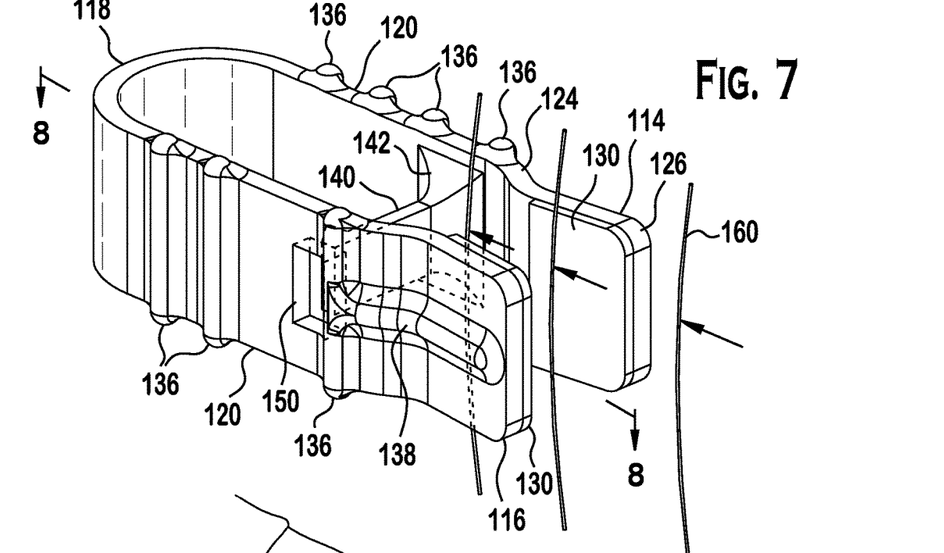
FIG. 7 is a perspective view of the vascular catheter wire clamp according to the invention showing portions of coil(s) of catheter wire being inserted there into.
Figure 8:
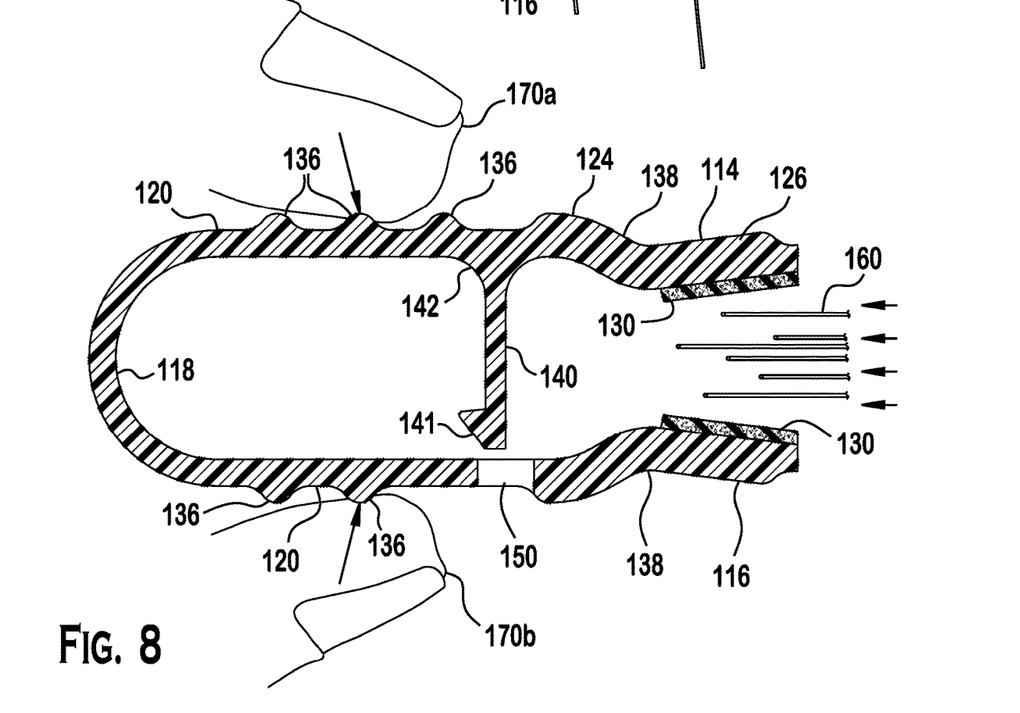
FIG. 8 is a cross section view of the vascular catheter wire clamp of FIG. 7 taken along line 8-8.
Figure 9:
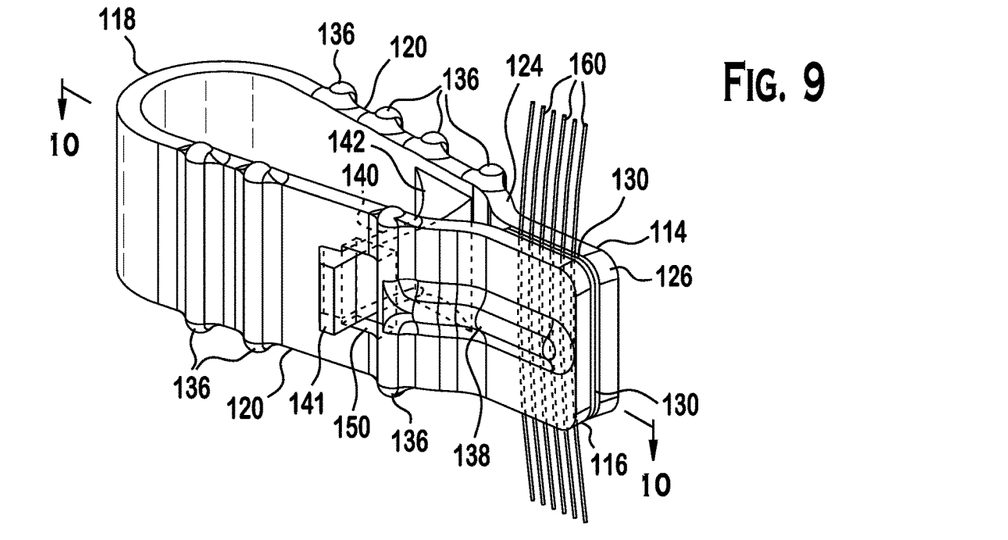
FIG. 9 is a perspective view of a vascular catheter wire clamp according to the invention showing portions of coil(s) of catheter wire clamped there upon.
Figure 10:
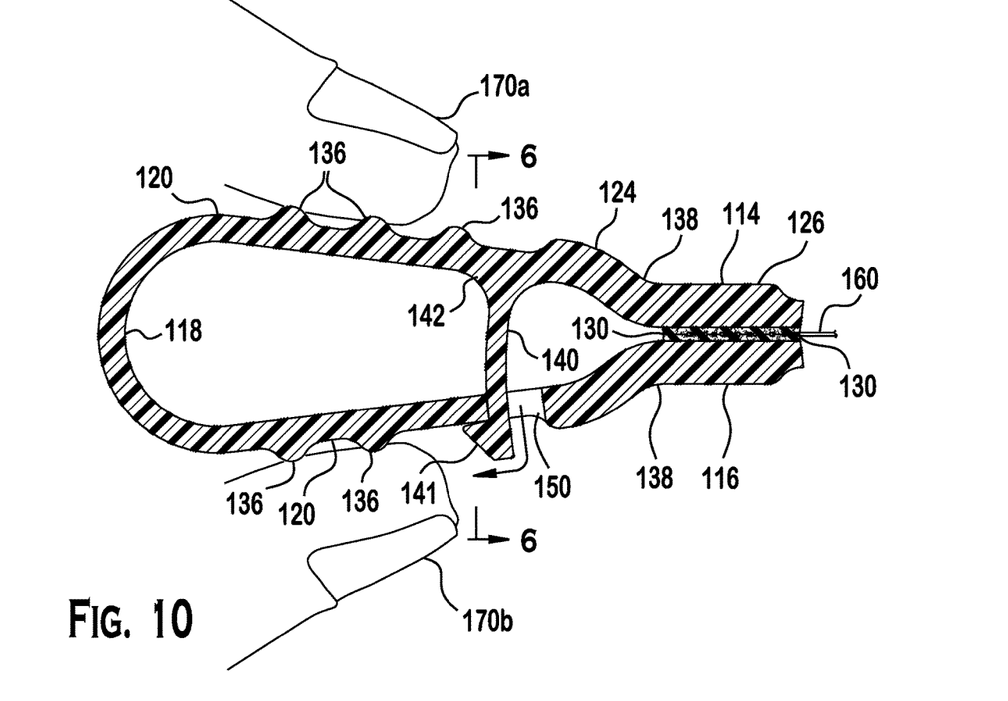
FIG. 10 is a cross section view of the vascular catheter wire clamp of FIG. 9 taken along line 10-10 showing portions of coil(s) of catheter wire secured after locking.

FIGS. 7 and 10 more specifically illustrate the positioning of fingers 170a, 170b to create the forces A and B to effect this deflection of the arms 114, 116 and clamping shaft 140.

Figure 11:
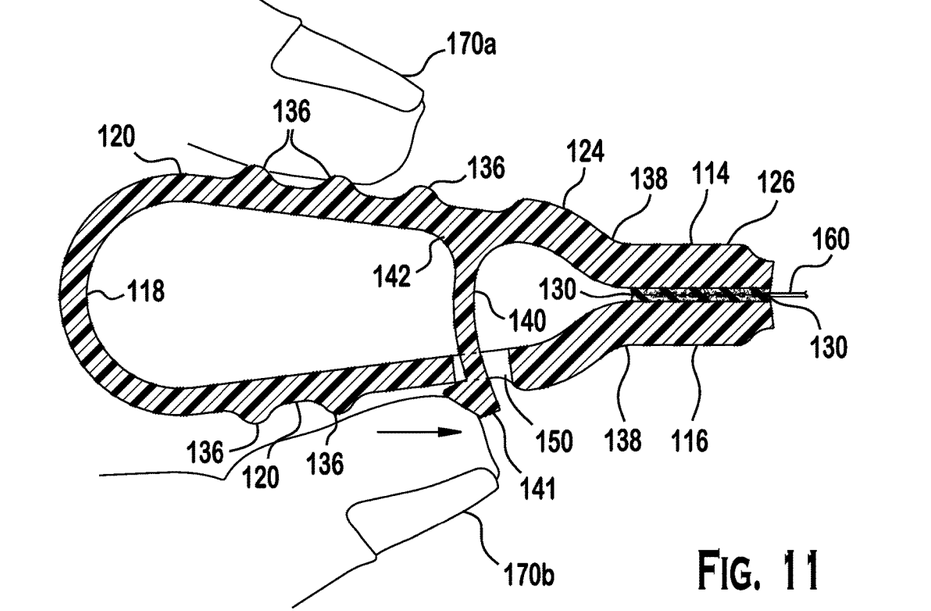
FIG. 11 is another cross section view of the vascular catheter wire clamp of FIG. 9 taken along line 10-10 showing portions of coil(s) of catheter wire being released during unlocking.
Figure 12:
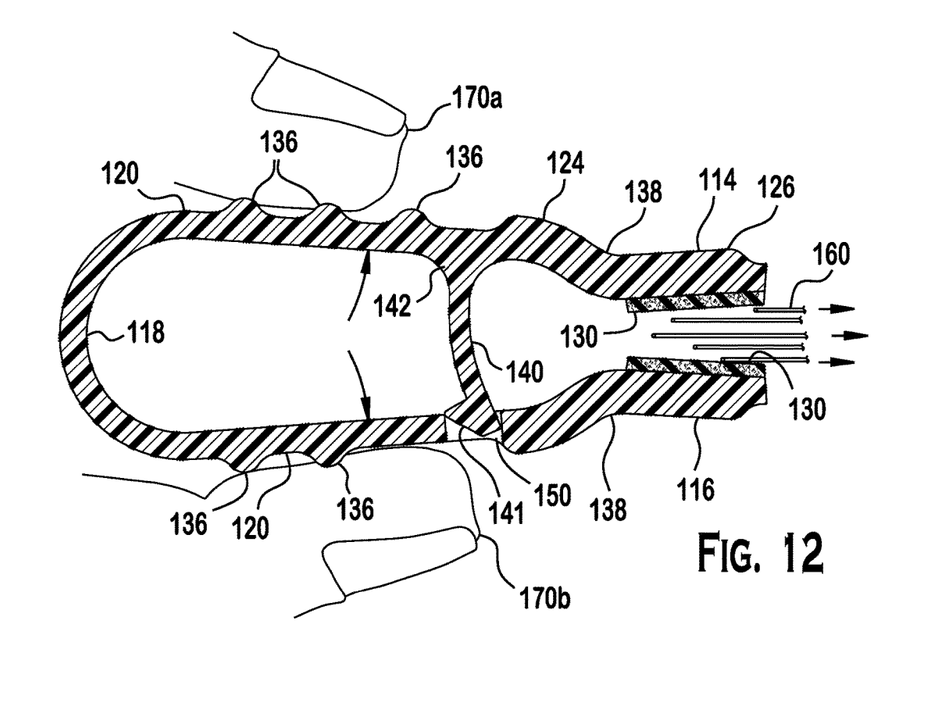
FIG. 12 is a cross section view of the vascular catheter wire clamp of FIG. 9 showing portions of coil(s) of catheter wire released after unlocking.

FIGS. 10, 11, and 12 are cross sections of clamp 100 that illustrate how an operator uses a force C to disengage ledge 141a from the proximal and outward facing edge of the second arm 116 to release the wires 160.

In an exemplary embodiment, the clamp 100 is used in a medical or veterinary procedure generally as follows:

An operator opens a package containing the clamp 100 but does not remove it from the packaging; the operator flushes the packaging, which contains the clamp 100, with saline solution. The operator then removes clamp 100 from the packaging, and the operator secures wires 160 with clamp 100. At the conclusion of the procedure, or when no longer needed, the clamp 100 is removed as described above and stored or thrown away.

The clamp 100 according to the invention may be at least one element in a kit which may include as one embodiment a set of clamps (which may be color coded), at least one set of gripping pads per included clamp, wire(s), catheter(s), and labeling material(s). Labeling materials suitable for use in surgical settings are those known to those of ordinary skill in the art and may include adhesive-backed paper or other writing surfaces and implements with which to write information on the labels.

The foregoing illustrates some of the possibilities for practicing the invention. Many other embodiments are possible within the scope and spirit of the invention. It is, therefore, intended that the foregoing description be regarded as illustrative rather than limiting, and that the scope of the invention is given by the appended claims together with their full range of equivalents.

What is claimed is:

1. A vascular catheter wire clamp, comprising:
   an elastic body having:
      a first arm having a first retention surface;
      a second arm having a second retention surface; and
      a bent section connecting the first arm and the second arm such that the first arm extends away from the bent section and parallel with the second arm, wherein each of the first arm and the second arm include a clasping section, a bridge section, and a retention section and wherein the bridge section extends from the clasping section and is angled toward a longitudinal axis L of the body and wherein the retention section is an elongated member that extends from the bridge section at an angle away from the longitudinal axis L of the body; and
   a clamping shaft extending inward from an inwardly facing surface of the first arm and having a retention member positioned along an end thereof; and
   a clamping shaft receiving passageway positioned through the second arm and corresponding with the clamping shaft and the retention member.

2. The vascular catheter wire clamp according to claim 1, further comprising a first gripping pad positioned along an inner surface of the first retention surface.

3. The vascular catheter wire clamp according to claim 2, further comprising a second gripping pad positioned along an inner surface of the second retention surface.

4. The vascular catheter wire clamp according to claim 3, wherein the body is a "U"-shaped monolithic member.

5. The vascular catheter wire clamp according to claim 4, wherein the first arm and the second arm are of equal lengths.

6. The vascular catheter wire clamp according to claim 4, wherein the bent section is "U" shaped.

7. The vascular catheter wire clamp according to claim 6, wherein the clasping section is an elongated member that extends from one end of the bent section.

8. The vascular catheter wire clamp according to claim 7, wherein the retention section of each of the first arm and the second arm is positioned opposite the bent section and the retention section of each of the first arm and the second arm includes an inner planar surface, wherein the first retention surface is formed on the inner planar surface of the first arm and the second retention surface is formed on the inner planar surface of the second arm.

9. The vascular catheter wire clamp according to claim 8, wherein the first retention surface of the first arm includes a first gripping pad and the second retention surface of the second arm includes a second gripping pad corresponding to the first gripping pad.

10. The vascular catheter wire clamp according to claim 9, wherein the first gripping pad and the second griping pad is a rectangular-shaped planar member having the same length and width as the first retention surface of the first arm and the second retention surface of the second arm, respectively.

11. The vascular catheter wire clamp according to claim 10, further comprising a plurality of gripping supports arranged crosswise and located on the outward facing surface of each of the first arm and the second arm.

12. The vascular catheter wire clamp according to claim 11, wherein the plurality of gripping supports are positioned between the bent section and the bridge section.

13. The vascular catheter wire clamp according to claim 12, further comprising a reinforcement rib located on an outward facing surface of the retention section.

14. The vascular catheter wire clamp according to claim 13, wherein the reinforcement rib is longitudinally oriented transverse to the plurality of gripping supports.

15. The vascular catheter wire clamp according to claim 1, wherein the bridge section extends from the clasping section at angle of approximately 30 degrees inward toward a longitudinal axis L of the body.

16. The vascular catheter wire clamp according to claim 15, wherein the retention section extends from the bridge section at the angle at approximately 30 degrees away from the longitudinal axis L of the body.

17. A vascular catheter wire clamp, comprising:
an elastic "U"-shaped monolithic body having:
a first arm having a first retention surface, the first retention surface having a rectangular-shaped planar first gripping pad of the same length and width as the first retention surface and positioned along an inner planar surface of the first retention surface;
a second arm having a second retention surface, the second retention surface having a rectangular-shaped planar second gripping pad of the same length and width as the second retention surface and positioned along an inner planar surface of the second retention surface; and
a bent "U" shaped section connecting the first arm and the second arm such that the first arm extends away from the bent section and parallel with the second arm, the first arm and the second arm of equal lengths, wherein each of the first arm and the second arm include a clasping section extending from one end of the bent section, a bridge section extending from the clasping section and angled at approximately 30 degrees inward toward a longitudinal axis L of the body, and a retention section extending from the bridge section and angled at approximately 30 degrees away from the longitudinal axis L of the body; and
a clamping shaft extending inward from an inwardly facing surface of the first arm and having a retention member positioned along an end thereof; and
a clamping shaft receiving passageway positioned through the second arm and corresponding with the clamping shaft and the retention member; and
each of the first arm and the second arm further comprising a plurality of gripping supports arranged crosswise and located on the outward facing surface of each of the first arm and the second arm positioned between the bent section and the bridge section, and each of the first arm and the second arm further comprising a reinforcement rib located on an outward facing surface of the retention section and longitudinally oriented transverse to the plurality of gripping supports.

* * * * *